United States Patent
Bernard et al.

(10) Patent No.: US 8,080,419 B2
(45) Date of Patent: Dec. 20, 2011

(54) PROCESS FOR RECYCLING SOLID SUPPORTS FOR CULTIVATION OF ANCHORAGE-DEPENDENT CELLS

(75) Inventors: Alain Bernard, Ville-la-Grand (FR); Frederic Papp, Les Evouettes (CH)

(73) Assignee: Ares Trading S.A., Aubonne (CH)

( * ) Notice: Subject to any disclaimer, the term of this patent is extended or adjusted under 35 U.S.C. 154(b) by 1326 days.

(21) Appl. No.: 10/580,777

(22) PCT Filed: Nov. 26, 2004

(86) PCT No.: PCT/EP2004/053133
§ 371 (c)(1), (2), (4) Date: Feb. 26, 2007

(87) PCT Pub. No.: WO2005/052136
PCT Pub. Date: Jun. 9, 2005

(65) Prior Publication Data
US 2007/0202597 A1 Aug. 30, 2007

Related U.S. Application Data

(60) Provisional application No. 60/526,414, filed on Dec. 2, 2003.

(30) Foreign Application Priority Data

Nov. 28, 2003 (EP) .................................. 03104440

(51) Int. Cl.
*C12M 3/04* (2006.01)
*C12N 5/00* (2006.01)
*C12N 1/20* (2006.01)
*C12Q 1/00* (2006.01)
*C12P 1/00* (2006.01)
*C12M 1/00* (2006.01)

(52) U.S. Cl. .............. 435/399; 435/4; 435/41; 435/243; 435/253.6; 435/289.1; 435/395

(58) Field of Classification Search .................. None
See application file for complete search history.

(56) References Cited

U.S. PATENT DOCUMENTS
5,266,476 A 11/1993 Sussman et al.
(Continued)

FOREIGN PATENT DOCUMENTS
EP 0 097 907 1/1984
(Continued)

OTHER PUBLICATIONS

New Brunswick Scientific "Fermentation & Cell Culture FAQs" Feb. 12, 2003 [online] <URL:http://www.nbsc.com/support/faqs/Default.asp#fibra>, 13 pages.*

(Continued)

*Primary Examiner* — Chris R Tate
*Assistant Examiner* — Aaron J Kosar
(74) *Attorney, Agent, or Firm* — Saliwanchik, Lloyd & Eisenschenk (57) ABSTRACT

This invention relates to methods for use in industrial production of proteins. Specifically, the present invention provides a method of recycling solid supports for cultivation of anchorage-dependent cells such as, e.g., microcarriers and Fibra-Cel® disks. Solid supports recycled by a method of the present invention allow obtaining a protein productivity level comparable to the productivity level obtained with non-recycled solid support. The method comprises the steps of rinsing with water, rinsing with a sodium hydroxide solution and second rinsing step with water.

28 Claims, 3 Drawing Sheets

System for cell cultivation

U.S. PATENT DOCUMENTS

2001/0021389 A1  9/2001 Starling et al.

FOREIGN PATENT DOCUMENTS

| JP | 04-126068 | 4/1992 |
| JP | 2002-171967 | 6/2002 |

OTHER PUBLICATIONS

New Brunswick Scientific (NBSC) "FIBRA-CEL Disks" Nov. 23, 2004 [online] <URL:http://www.nbsc.com/products/miscellaneous/fibracel/>, 3 pages.*

Beltrán-Langarica, A; López-Contreras, D; and Kuri-Harcuch, W "A Simple Procedure for Washing and Sterilizing Plastic Tissue Culture Dishes for Reuse" Methods in Cell Science, 1983, 8(4), pp. 173-176.*

Galin, et al "Studies of Residual Alkali on Intraocular Lenses Sterilized with NaOH" J Am Intraocul Implant Soc, 1983 Summer, 9(3), pp. 290-292.*

Sanborn, M.R; Wan, S.K.; Bulard, R. "Microwave Sterilization of Plastic Tissue Culture Vessels for Reuse" Applied and Environmental Microbiology, Oct. 1982, 44(4), pp. 960-964.*

Bohak, Z. et al. "Novel Anchorage Matrices for Suspension Culture of Mammalian Cells", *Biopolymers*, 1987, pp. S205-S213, vol. 26, Suppl.

Buck, C. D. et al. "Growth of Brown Bullhead (BB) and Other Fish Cell Lines on Microcarriers and the Production of Channel Catfish Virus (CCV)", *Journal of Virological Methods*, 1985, pp. 171-184, vol. 10, No. 2.

Ikonomou, L. et al. "Microcarrier Culture of Lepidopteran Cell Lines: Implications for Growth and Recombinant Protein Production", *Biotechnol. Prog.*, 2002, pp. 1345-1355, vol. 18, No. 6.

Petti, S. A. et al. "Three-Dimensional Mammalian Cell Growth on Nonwoven Polyester Fabric Disks", *Biotechnol. Prog.*, 1994, pp. 548-550, vol. 10, No. 5.

Sabu, A. et al. "Continuous Production of Extracellular $_L$-Glutaminase by Ca-Alginate-Immobilized Marine *Beauveria bassiana* BTMF S-10 in Packed-Bed Reactor", *Applied Biochemistry and Biotechnology*, 2002, pp. 71-79, vols. 102-103, Nos. 1-6.

Wang, G. et al. "Modified CelliGen-Packed Bed Bioreactors for Hybridoma Cell Cultures", *Cytotechnology*, 1992, pp. 41-49, vol. 9, Nos. 1-3.

* cited by examiner

System for cell cultivation

PROCESS FOR RECYCLING SOLID SUPPORTS FOR CULTIVATION OF ANCHORAGE-DEPENDENT CELLS

FIELD OF THE INVENTION

This invention relates to methods for use in industrial production of proteins. Specifically, the present invention provides a method of recycling so lid supports for cultivation of anchorage-dependent cells such as, e.g., microcarriers and Fibra-Cel® disks. Solid supports recycled by a method of the present invention allow obtaining a protein productivity level comparable to the productivity level obtained with non-recycled solid supports.

BACKGROUND OF THE INVENTION

The increasing demand for therapeutic proteins produced in mammalian expression systems has led in the past 30 years to significant advances in the areas of in vitro cell cultivation, scale-up, expression vectors and medium development.

While ordinary suspension cultures are suitable for growth of certain mammalian cell lines, many cells are anchorage-dependent, and require a solid surface in order to proliferate, metabolize nutrients and produce biomolecules. Conventional means for growth of these cells on a small scale include petri-dishes, flasks and roller bottles. A number of approaches have been taken by various investigators to develop packed bed bioreactors with large surface-area-to-volume ratios for space and operational economy. Another approach is to culture cells on a packing material inside a column shaped vessel that is linked to a bioreactor (Wang et al. 1992).

The use of solid supports such as microcarriers or Fibra-Cel® disks in bioreactor systems increases the available growth area for anchorage-dependent cells per unit of volume and results in obtaining satisfactory protein productivity. Microcarriers and Fibra-Cel® disks are thus routinely used in animal cell culture for the growth of anchorage-dependent cells and are among the established technological platforms for industrial production of proteins (see, e.g., Buck and Loh, J. Viriological Meth., 1985; Bohak et al, Biopolymers, 1987; Petti et al, Biotechnol. Prog., 1994; Ikonomou et al, Biotechnol. Prog, 2002).

Microcarriers are small solid particles on which cells may be grown in suspension culture. Cells are capable of adhering and propagating on the surface of microcarriers. Typically, microcarriers consist of beads, the diameter of which is comprised between 90 µm and 300 µm. Microcarriers can be made of various materials that have proven successful for cell attachment and propagation such as, e.g., glass, polystyrene, polyethylene, dextran, gelatin and cellulose. In addition, the surface of microcarriers may be coated with a material promoting cell attachment and growth such as, e.g., e.g., N,N-diethylaminoethyl, glass, collagen or recombinant proteins. Both macroporous and non-porous microcarriers do exist. Macroporous surfaces give the cells easy access to the interior of the microcarrier after inoculation, and once inside of the microcarrier, the cells are protected from the shear forces generated by mechanical agitation and aeration in the bioreactor.

Fibra-Cel® disks (New Brunswick Scientific) are disks of 6 mm in diameter that are composed of polyester non-woven fiber bonded to a sheet of polypropylene mesh (see, e.g., U.S. Pat. No. 5,266,476). Fibra-Cel® disks are usually treated electrostatically to facilitate suspension cells adhering to the disks and becoming trapped in the fiber system, where they remain throughout the cultivation process. Cell density and productivity achieved with cells grown on Fibra-Cel ® disks can be up to ten times higher than with cells growing on microcarriers.

Currently, Fibra-Cel® disks and microcarriers are not re-used. However, using new solid supports for each protein production phase is expensive. In addition, changing the solid support after each protein production phase is time-consuming. Accordingly, there is a need for a method of recycling solid supports for cultivation of anchorage-dependent cells in situ, said method allowing maintaining a protein productivity level comparable to the protein productivity level obtained with non-recycled supports.

SUMMARY OF THE INVENTION

The present invention provides methods of recycling solid supports for cultivation of anchorage-dependent cells in situ. The methods of the present invention allow maintaining a protein productivity level comparable to the protein productivity level obtained with non-recycled supports. The methods of the present invention improve the protein production process both in terms of cost and in terms of overall efficiency.

Accordingly, a first aspect of the present invention is directed to a method of recycling a solid support for cultivation of anchorage-dependent cells located within a system for cell cultivation comprising the steps of:
  a) emptying said system of liquid;
  b) rinsing said system with an aqueous solution;
  c) rinsing said system with a sodium hydroxide solution; and
  d) rinsing said system with an aqueous solution.

A second aspect of the present invention relates to a solid support for cultivation of anchorage-dependent cells recycled according to a method of the present invention.

A third aspect relates to the u se of such a solid support recycled according to a method of the present invention for cultivation of cells.

DETAILED DESCRIPTION OF THE INVENTION

The present invention stems from the finding of a method of recycling solid supports for cultivation of anchorage-dependent cells in situ. As shown in Example 3, said method allows maintaining a protein productivity level with recycled supports comparable to the protein productivity level obtained with non-recycled supports.

A first aspect of the present invention is directed to a method of recycling a solid support for cultivation of anchorage-dependent cells located within a system for cell cultivation comprising the steps of:
  a) emptying said system of liquid;
  b) rinsing said system with an aqueous solution;
  c) rinsing said system with a sodium hydroxide solution; and
  d) rinsing said system with an aqueous solution.

As used herein, the terms "re-use" and "recycle" are considered to be synonymous and can be used interchangeably throughout the disclosure.

As used herein, the term "rinse" refers to a method comprising the steps of:
(i) filling a device with a liquid;
(ii) incubating said liquid in said device; and
(iii) emptying said device of said liquid.

Preferably, the liquid is circulating in the device during step (ii).

A preferred embodiment is directed to such a method of recycling a solid support for cultivation of anchorage-dependent cells wherein said aqueous solution is water.

Another preferred embodiment is directed to such a method of recycling a solid support for cultivation of anchorage-dependent cells wherein the sodium hydroxide solution is at a concentration within a range of about 1% to about 3% sodium hydroxide. Preferably, said concentration is within a range of about 1.5% to about 2.5% sodium hydroxide. Most preferably, said concentration is about 2% sodium hydroxide.

In still another preferred embodiment, the present invention is directed to a method of recycling a solid support for cultivation of anchorage-dependent cells wherein step (c) is carried out by filling the system with a sodium hydroxide solution at a desired concentration of sodium hydroxide. In another preferred embodiment, step (c) is carried out by filling the system with water and by adding a concentrated sodium hydroxide solution to reach a desired concentration of sodium hydroxide within the system. The desired concentration of sodium hydroxide is preferably within a range of about 1% to about 3% sodium hydroxide. More preferably, desired concentration of sodium hydroxide is within a range of about 15% to about 2.5% sodium hydroxide. Most preferably, said desired concentration of sodium hydroxide is about 2% sodium hydroxide.

Another preferred embodiment is directed to a method of recycling a solid support for cultivation of anchorage-dependent cells according to the invention wherein step (d) is performed at least two times. Preferably, step (d) is performed at least three times. More preferably, step (d) is performed three times. Most preferably, step (d) is performed five times.

One embodiment of the invention is directed to the above method of recycling a solid support for cultivation of anchorage-dependent cells wherein the aqueous solution in step (b) is Water For Injection (WFI). Alternatively, step (b) may be performed with Purified Water.

Another embodiment of the invention is directed to the above method of recycling a solid support for cultivation of anchorage-dependent cells wherein the aqueous solution in step (d) is Water For Injection. Alternatively, step (d) is performed with Purified Water. Most preferably, when step (d) is performed at least twice, all rinses except the last one are performed with Purified Water, and the last rinse is performed with Water For Injection.

The terms "Purified Water (PW)" and "Water for Injection (WFI)" are well-known by those of skill in the art For example, the US Pharmacopeia (USP) and the European Agency for the Evaluation of Medicinal Products (EMEA) disclose standards and recommendations for the bacteriological purity and for the chemical quality of PW and WFI.

As used throughout the specification, the term "solid support for cultivation of anchorage-dependent cells" refers to a material for the growth of cells that require attachment to a solid surface in order to efficiently proliferate, metabolize nutrients, and/or produce proteins.

In one embodiment of the present invention, the solid support for cultivation of anchorage-dependent cells is made, e.g., of non-woven fibrous matrix bonded to a porous support sheet. Such supports can be made according to U.S. Pat. No. 5,266,476. Preferably, such supports comprise a matrix that is a physiologically acceptable three-dimensional network of fibers in the form of a sheet having a pore volume as a percentage of total volume of from 40 to 95% and a pore size of from 10 microns to 100 microns, the overall height of the matrix being from 50 microns to 500 microns. The matrix may for example be made of fibers selected from the group consisting of flat, non-round, and hollow fibers and mixtures thereof, said fibers being of from 0.5 microns to 50 microns in diameter or width. Alternatively, the material of the matrix may be selected from the group consisting of polyesters, polyalkylenes, polyfluorochloroethylenes, polyvinyl chloride, polystyrene, polysulfones, cellulose acetate, glass fibers, and inert metal fibers. The support may be, e.g., in a shape selected from the group consisting of squares, rings, discs, and cruciforms. More preferably, the matrix is comprised of non-woven polyester and the support is comprised of a sheet of polypropylene mesh with substantially square mesh opening of about one square millimeter. In a most preferred embodiment, the solid support is a disk made of non-woven polyester bonded to a sheet of polypropylene mesh. Such supports are commercialized under the name of Fibra-Cel® disks (New Brunswick Scientific).

In another embodiment of the present invention, the solid support for cultivation of anchorage-dependent cells is a microcarrier. Numerous microcarriers are well-known in the art and commercially available. The microcarrier may for example be made of a material selected from the group consisting of polyester (e.g. BioNOCII™), polystyrene (e.g., Biosilon®, Nunc; 2D MicroHex®, Nunc; SoloHill's microcarriers), polyethylene weighted with silica (e.g., Cytoline®, Amersham), glass (e.g., G-2892, Sigma), gelatin (e.g., Cultispher®, Hyclone), cellulose (e.g., Cytopre®, Amersham) and dextran (e.g., Cytodex®, Amersham). In addition, the microcarrier may be coated. The microcarrier may for example be coated with a material selected from the group consisting of glass (e.g., SoloHill's glass-coated microcarriers), N,N-diethylaminoethyl (e.g., Cytodex®1, Amersham), collagen (e.g., Cytodex®3, Amersham) and recombinant proteins (e.g., ProNectin®, SoloHill). In one preferred embodiment, the microcarrier is a macroporous microcarrier such as, e.g., Cytopore® or Cultispher®. In another preferred embodiment, the microcarrier is a non-porous support such as, e.g., glass beads, Cytodex®, Biosilon® or 2D MicroHex®.

As used throughout the specification, the term "a system for cell cultivation" refers to a device or several connected devices in which cells are cultivated.

In one embodiment, such a system comprises a bioreactor. The term "bioreactor" refers to an apparatus or closed container that is used for generating biomolecules such as secreted proteins using the synthetic or chemical conversion capacity of a cell. Bioreactors include classical fermentors and cell culture perfusion systems. Bioreactors allow controlling various parameters during the cell culture process such as, e.g., the circulation loop flow, the temperature, the overpressure and/or the medium perfusion rate.

In one preferred embodiment, the system for cell cultivation is designed for comprising a packed bed of microcarriers or of Fibra-Cel® disks within the bioreactor. Typically, such bioreactors comprise an internal column in which the solid support for cultivation of anchorage-dependent cells is located.

In one preferred embodiment, the system for cell cultivation further comprises an external column connected to the bioreactor. In this embodiment, the bioreactor is used as a media-conditioning tank, with the cells grown and propagated in the external column. Such systems comprising external columns may be designed, e.g., according to Example 1.1. and/or as described in Wang et al. (*Cytotechnology*, 1992). The connection between the external column and the bioreactor preferably comprises a circulation pump.

The solid support for cultivation of anchorage-dependent cells may be located either within the bioreactor or within the external column. When using a system for cell cultivation comprising an external column, the solid support is preferably located within the external column. When using a system for cell cultivation without external column, the system preferably comprises a bioreactor comprising an internal column in which the solid support is located.

Figure 3:
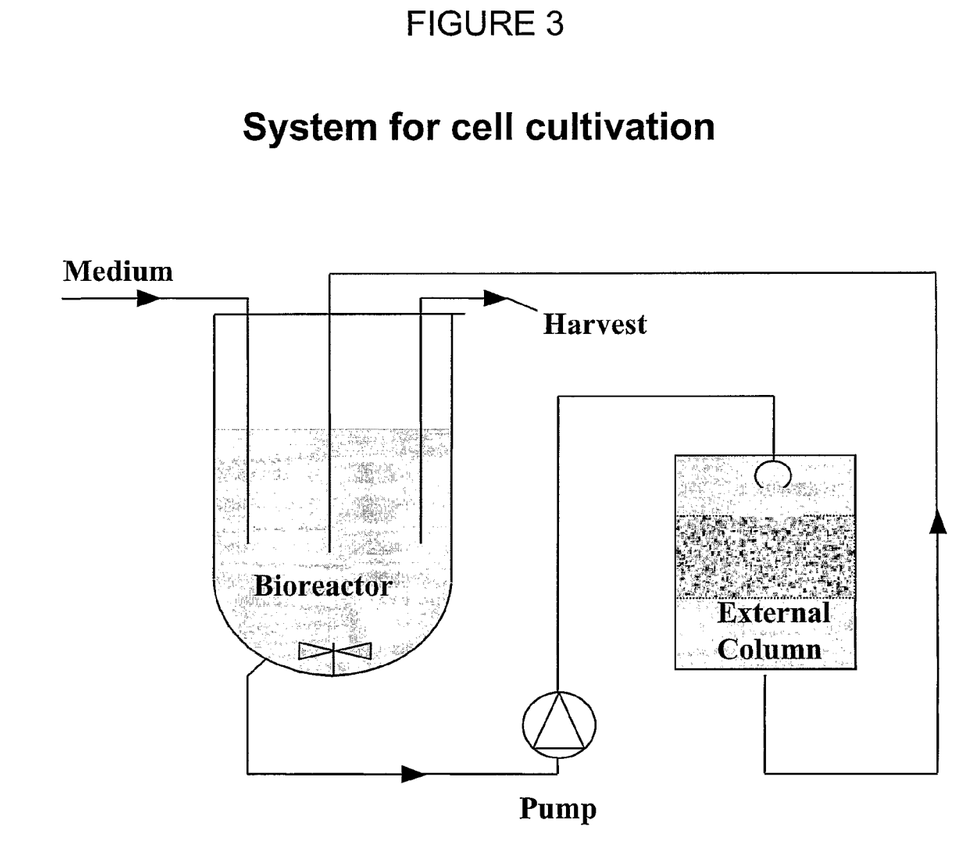
FIG. 3 shows a system for cell cultivation suitable for performing the methods of the present invention.

In a most preferred embodiment of the present invention, the system for cell cultivation comprises an external column connected to a bioreactor, wherein the solid support for cultivation of anchorage-dependent cells is located within the external column, and wherein the connection between the external column and the bioreactor comprises a circulation pump. Such a system is illustrated on FIG. 3. Such systems are particularly advantageous in the frame of the present invention since using such systems allows efficient circulation of rinsing solutions through the packed bed external column. In another most preferred embodiment, the system for cell cultivation comprises a bioreactor comprising an internal column, wherein the solid support for cultivation of anchorage-dependent cells is located within said internal column.

In one embodiment, the system for cell cultivation is sterilized after performing step (d).

When using a system for cell cultivation comprising an external column, the external column may be removed from the system after performing step (d). Accordingly, in another embodiment the external column is sterilized after performing step (d).

In a preferred embodiment, step (d) is carried out with a circulation loop flow within a range of about 500 $l·h^{-1}kg^{-1}$ to about 700 $l·h^{-1}kg^{-1}$. Preferably, said circulation loop flow is within a range of about 550 $l·h^{-1}kg^{-1}$ to about 650 $l·h^{-1}kg^{-1}$. Most preferably, said circulation loop flow is of about 583 $l·h^{-1}kg^{-1}$.

In a further preferred embodiment, step (d) is carried out at ambient temperature. Typically, the ambient temperature is within a range of about 15° C. to about 30° C.

In a further preferred embodiment, step (d) is carried out under an overpressure within a range selected from the group consisting of:
  (i) about 100 millibars to about 900 millibars;
  (ii) about 200 millibars to about 800 millibars;
  (iii) about 300 millibars to about 700 millibars; and
  (iv) about 400 millibars to about 600 millibars;
Preferably, said overpressure is of about 500 millibars.

Alternatively, step (d) may be carried out under an overpressure within a range either of about 100 millibars to about 300 millibars, or of about 150 millibars to about 250 millibars. Step (d) may for example be carried out under an overpressure of about 200 millibars.

In a further preferred embodiment, step (d) is carried out for a duration within a range of about 5 minutes to about 30 minutes. Preferably, said duration is within a range of about 5 minutes to about 20 minutes. Most preferably, said duration is of about 10 minutes.

In another preferred embodiment, step (c) is carried out with a circulation loop flow within a range of about 500 $l·h^{-1}kg^{-1}$ to about 700 $l·h^{-1}kg^{-1}$. Preferably, said circulation loop flow is within a range of about 550 $l·h^{-1}kg^{-1}$ to about 650 $l·h^{-1}kg^{-1}$. Most preferably, said circulation loop flow is of about 583 $l·h^{-1}kg^{-1}$. Preferably, step (c) is carried out for a duration within a range of about 20 minutes to about 40 minutes. More preferably, said duration is within a range of about 25 minutes to about 35 minutes. Most preferably, said duration is of about 30 minutes.

Alternatively, step (c) may be carried out with a circulation loop flow set at an initial value within a range of about 100 $l·h^{-1}kg^{-1}$ to about 300 $l·h^{-1}kg^{-1}$, or within a range of about 150 $l·h^{-1}kg^{-1}$ to about 250 $l·h^{-1}kg^{-1}$, or of 215 $l·h^{-1}kg^{-1}$, and the circulation loop flow is progressively increased to a final value within a range of about 500 $l·h^{-1}kg^{-1}$ to about 700 $l·h^{-1}kg^{-1}$, or within a range of about 550 $l·h^{-1}kg^{-1}$ to about 650 $l·h^{-1}kg^{-1}$, or at 583 $l·h^{-1}kg^{-1}$. Then the circulation loop flow is maintained at the final value for a duration within a range of about 20 minutes to about 40 minutes. More preferably, said duration is within a range of about 25 minutes to about 35 minutes. Most preferably, said duration is of about 30 minutes.

In still another preferred embodiment, step (c) is carried out at a temperature within a range of about 50° C. to about 70° C. Preferably, said temperature is within a range of about 55° C. to about 65° C. Most preferably, said temperature is of about 60° C.

A preferred embodiment of the present invention is directed to a method of recycling a solid support for cultivation of anchorage-dependent cells wherein step (b) is carried out at a temperature within a range of about 50° C. to about 70° C. Preferably, said temperature is within a range of about 55° C. to about 65° C. Most preferably, said temperature is of about 60° C.

In yet a further preferred embodiment, step (b) is carried out under an overpressure within a range selected from the group consisting of:
  (i) about 100 millibars to about 900 millibars;
  (ii) about 200 millibars to about 800 millibars;
  (iii) about 300 millibars to about 700 millibars; and
  (iv) about 400 millibars to about 600 millibars;
Preferably, said overpressure is of about 500 millibars.

Alternatively, step (b) is carried out under an overpressure within a range of about 200 millibars to about 400 millibars, or within a range of about 250 millibars to about 350 millibars. The overpressure may for example be of about 300 millibars.

In another preferred embodiment, step (b) is carried out for a duration within a range of about 5 minutes to about 30 minutes. Preferably, said duration is within a range of about 5 minutes to about 20 minutes. Most preferably, said duration is of about 10 minutes.

Many variations and/or adaptations may be applied by the man of skill in the art to the temperature, the overpressure, the circulation loop flow and the duration for/at which steps (b) to (d) are carried out. For example, flow rates may vary depending on (i) the type of solid support for cultivation of anchorage-dependent cells; and (ii) the porosity of the solid support. Further, carrying out step (b) and (d) under overpressure is not an absolute requirement. However, it is good practice to minimize risk of contamination.

Alternatively, solid supports for cultivation of anchorage-dependent cells may be recycled ex situ in a method comprising the steps of:
  a) removing the solid support from a system for cell cultivation;
  b) rinsing said solid support with an aqueous solution;
  c) rinsing said solid support with a sodium hydroxide solution; and
  d) rinsing said solid support with an aqueous solution.

A second aspect of the present invention is directed to a solid support for cultivation of anchorage-dependent cells recycled according to a method of the present invention.

A third aspect of the present invention is directed to the use of a solid support recycled according to a method of the present invention for cultivation of cells.

The cells may be of, e.g., animal, insect or microbial origin. As used herein, the term "animal cell" includes human and non-human mammalian cells, non-mammalian cells, recombinant cells and hybridomas. Examples of mammalian cells that can be cultivated using a solid support according to the present invention include, e.g., 3T3 cells, COS cells, human osteosarcoma cells, MRC-5 cells, BHK cells, VERO cells, CHO cells, rCHO-tPA cells, rCHO-Hep B Surface Antigen cells, HEK 293 cells, rHEK 293 cells, rC127-Hep B Surface Antigen cells, Normal Human fibroblast cells, Stroma cells, Hepatocytes cells and PER.C6 cells. Examples of hybridomas that can be cultivated using a solid support according to the present invention include, e.g., DA4.4 cells, 123A cells, 127A cells, GAMMA cells and 67-9-B cells. Examples of insect cells that can be cultivated using a solid support according to the present invention include, e.g., lepidopteran cells, Tn-368 cells, SF9 cells, rSF9 cells and Hi-5 cells (see, e.g., Ikonomou et al. 2002). Examples of non-mammalian cells that can be cultivated using a solid support according to the present invention include, e.g., brown bullhead cell lines (see, e.g., Buck et al. 1985). Examples of microorganisms that can be cultivated using a solid support according to the present invention include, e.g., *Coniothyrium minitans, Kluyveromyces lactis, Phanerochaete chrysosporium, Scedosporium apiospermum, Cephalospodum acremonium* and *Beauveria bassiana* (see, e.g.,Sabu et al, *Appl.Biochem.Biotechnol.*, 2002.

In a preferred embodiment, the cell is a mammalian cell Cultivation of mammalian cells is an established process for production of therapeutic proteins. Therapeutic proteins that may be produced using a solid support recycled according to a method of the present invention include, e.g., chorionic gonadotropin, follicle-stimulating hormone, lutropin-chorio­gonadotropic hormone, thyroid stimulating hormone, human growth hormone, interferons (e.g., interferon beta-1a, interferon beta-1b), interferon receptors (e.g., interferon gamma receptor), TNF receptors p55 and p75, TACI-Fc fusion proteins, interleukins (e.g., interleukin-2, interleukin-11), interleukin binding proteins (e.g., interleukin-18 binding protein), anti-CD11a antibodies, erythropoietin, granulocyte colony stimulating factor, granulocyte-macrophage colony-stimulating factor, pituitary peptide hormones, menopausal gonadotropin, insulin-like growth factors (e.g., somatomedin-C), keratinocyte growth factor, glial cell line-derived neurotrophic factor, thrombomodulin, basic fibroblast growth factor, insulin, Factor VIII, somatropin, bone morphogenetic protein-2, platelet-derived growth factor, hirudin, epoietin, recombinant LFA-3/IgG1 fusion protein, glucocerebrosidase, and muteins, fragments, soluble forms, functional derivatives, fusion proteins thereof.

In one embodiment, the cells are anchorage-dependent. In another embodiment, the cells are not anchorage-dependent. Actually, suspension cells can also be propagated on microcarriers and on supports made of non-woven fibrous matrix bonded to a porous support sheet such as Fibra-Cel®. The density of suspension cells propagated on such supports is even greater that the density that can be attained in suspension cultures.

Having now fully described this invention, it will be appreciated by those skilled in the art that the same can be performed within a wide range of equivalent parameters without departing from the spirit and scope of the invention and without undue experimentation.

While this invention has been described in connection with specific embodiments thereof, it will be understood that it is capable of further modifications. This application is intended to cover any variations, uses or adaptations of the invention following, in general, the principles of the invention and including such departures from the present disclosure as come within known or customary practice within the art to which the invention pertains and as may be applied to the essential features hereinbefore set forth as follows in the scope of the appended claims. For example, flow rates may vary depending on (i) the type of solid support for cultivation of anchorage-dependent cells; and (ii) the porosity of the solid support. Further, the overpressure is not an absolute requirement, but good practice to minimize risk of contamination.

All references cited herein, including journal articles or abstracts, published or unpublished patent application, issued patents or any other references, are entirely incorporated by reference herein, including all data, tables, figures and text presented in the cited references. Additionally, the entire contents of the references cited within the references cited herein are also entirely incorporated by reference.

Reference to known method steps, conventional methods steps, known methods or conventional methods is not any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various application such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

EXAMPLES

Example 1

Cell Culture Process 1.1. Equipment

All experiments were performed with systems composed of a bioreactor connected to an external column The configuration of the bioreactors was similar to the configuration of 40 liters Free-Standing Laboratory bioreactors manufactured by New MBR. The volume of the bioreactors and columns that were used are summarized in Table 1 below.

TABLE 1

| Bioreactor volume | Column volume | Mass of Fibra-Cel disks |
|---|---|---|
| 15-liter | 5.5-liter | 0.6-kg |
| 40-liter | 60 to 120-liter | 6.6 to 13.2-kg |
| 350-liter | 120 to 240-liter | 13.2 to 26.4-kg |

The external columns were made of inox 316L, with a Ra of 0.6 µm. The Ra describes the average surface roughness and is defined as an integral of the absolute value of the roughness profile measured over an evaluation length:

$$Ra = \frac{1}{l}\int_0^l |z(x)|dx$$

The external columns were packed with Fibra-Cel® disks (New Brunswick Scientific) according to the mass of carriers given in Table 1.

1.2. Cell Lines and Media
   1.2.1. Cell Lines

All experiments were performed with a CHO cell line producing a protein corresponding to the soluble extracellular portion of the p55 TNF receptor (SwissProt Accession No. P19438). The produced protein, designated r-hTBP-1, comprises amino acids 41 to 201 of SwissProt Accession No. P19438.

The r-hTBP-1-producing cell line was generated by transfecting CHO-DUKX cells with a vector comprising a cDNA encoding r-hTBP-1 and appropriate expression elements. Transfected clones were selected and a stably r-hTBP-1 expressing cell line was established.

1.2.2. Media

The medium used for cell cultivation was the Sigma C1850 medium.

1.3. Inoculation, Growth and Production Conditions

The culture process, also referred to as "run", comprises an inoculation step, a growth phase and a production phase.

1.3.1. Inoculation Conditions

When performing Example 3, $1.6 \cdot 10^9$ viable r-hTBP-1-producing cells per kilogram of Fibra-Cel® discs were transferred to the bioreactor, and when performing Example 4, at least $2.7 \cdot 10^9$ were transferred. The pump circulation being on during inoculation, the cells naturally attach to the Fibra-Cel® discs.

The Initial set-points for the conditioning tank control unit were as follows:
   Temperature: 37.0° C.
   Dissolved oxygen (DO): 50% air saturation
   pH: 7.00
   Bioreactor overpressure: 0.2 bar
   When performing Example 3: Agitation: 20 rpm.

1.3.2. Growth Conditions

During the growth phase, the bioreactor was operated in batch mode until the second day and then the dilution rate was progressively increased until a maximal value of 100 liters of perfused medium per day per kilogram of Fibra-Cel® disks (100 $l \cdot day^{-1} kg^{-1}$ of Fibra-Cel®). The pump circulation flow was progressively increased from 150 $l \cdot h^{-1}$ to 350 $l \cdot h^{-1}$ when performing Example 3, and from 150 $l \cdot h^{-1} kg^{-1}$ to 800 $l \cdot h^{-1} kg^{-1}$ when performing Example 4. On the eleventh day, the dissolved oxygen (DO) set-point was increased to 70% air saturation.

1.3.2. Production Conditions

Once the Glucose Consumption Rate (GCR) was superior to 150 $g \cdot day^{-1} kg^{-1}$ of Fibra-Cel®, the perfusion level was reduced to 18 liters of perfused medium per day (30 $l \cdot day^{-1} kg^{-1}$ of Fibra-Cel®) when performing Example 3, and to at least 10 liters of perfused medium per day per kilogram of Fibra-Cel® disks (at least 10 $l \cdot day^{-1} kg^{-1}$ of Fibra-Cel®) when performing Example 4. The production phase lasted 60 days.

Example 2

Analytical Methods 2.1. Measurement of the Total Organic Carbon (TOC)

Total organic carbon (TOC) is an indirect measure of organic molecules present in pharmaceutical water measured as carbon. TOC is commonly used as a process control attribute to monitor the performance of unit operations comprising the purification and distribution system. TOC allows determining whether all organic molecules have been removed after cleaning. A number of methods exist for analyzing TOC (see, e.g., European Pharmacopeia, 4th Edition, 2002, Chapter 2.2.44).

The TOC was measured using a Phoenix 8000 apparatus (Dohrmann) according to a protocol derived from the manufacturer's instructions. The TOC was expressed in parts per million (ppm).

2.2. Measurement of the *Limulus amebocyte* Lysate (LAL)

The *Limulus Amebocyte* Lysate (LAL) test is a test to detect or quantify bacterial endotoxins that may be present in or on a sample to which the test is applied. It uses *Limulus Amebocyte* Lysate obtained from the aqueous extracts of circulating amebocytes of horseshoe crab (*Limulus polyphemus* or *Tachypleus tridentatus*) which has been prepared and characterized for use as a LAL Reagent (see, e.g., Pharmacopeia of the United States of America, Twenty-Sixth Revision, Chapter 85)

The LAL was measured using a LAL Kinetic System comprising the WinKQCL® Software (Biowhittaker) according to a protocol derived from the manufacturer's instructions. The LAL was expressed in Endotoxin Units per millilitre ($EU \cdot ml^{-1}$).

2.3. Measurement of the Bio Burden

The Bio Burden is a measure of the level of viable microorganisms present in or on a sample. Bio Burden is also referred to as "Total Viable Aerobic Count". Numerous methods for measuring Bio Burden are available (see, e.g., European Pharmacopea, 4th Edition, 2002 Chapter 2.6.12).

The Bio Burden was tested by membrane filtration (see the European Pharmacopea, 4th Edition, 2002 Chapter 2.6.12). The membrane filters were incubated on petri-dishes comprising the following media:
   Trypcase-soja agar;
   Trypcase-soja agar+0.07% Lecithin+0.5% Tween 80; or
   Trypcase-soja agar+5% sheep blood.

The plates were incubated during 5 days at 32.5° C. The Bio Burden was expressed in number of colony-forming units per millilitre ($CFU \cdot ml^{-1}$).

2.4. Measurement of the Cumulative Productivity of r-hTBP-1

The Cumulative Productivity (CP), expressed in g of r-hTBP-1 per Kg of Fibra-Cel®, was calculated as follows: CP=(CP of the day before)+((r-hTBP-1 Titer of the day× Perfusion/mass of Fibra-Cel® in Kg)/1000×(time between the day before and the current day in hour)).

The perfusion was expressed in liters per 24 h. The r-hTBP-1 titer was expressed in mg per liter. The r-hTBP-1 titer was measured by an immunoenzymometric assay (IEMA), using the Serozyme kit from BioChem ImmunoSystems (Germany) and monoclonal anti-r-hTBP-1 antibodies.

2.5. Measurement of the Glucose Consumption Rate (GCR)

The glucose consumption rate (GCR), expressed in grams of glucose consumed per day per kg of Fibra-Cel®, was calculated as follows: GCR=((($G_{in}$–$G_{bioreactor}$)×Perfusion+($G_{bioreacor}$ of the day before–$G_{bioreactor}$ of the day)×((working volume in liters/time between the day before and the current day in hour)/mass of Fibra-Cel).

$G_{in}$ corresponds to the glucose concentration of the medium perfused into the system, expressed in grams per litre. $G_{bioreactor}$ corresponds to the glucose concentration of the medium within the bioreactor The perfusion was expressed in liters per 24 h. The working volume corresponds to the volume in liters of the culture in the system. Mass of Fibra-Cel is expressed in Kg Example 3

Recycling Protocol and Results 3.1. Recycling

The system was composed of a 15 liters bioreactor connected to a 5.5 liters external column as described in Example 1.1.

At the end of a run carried out with non-recycled Fibra-Cel® disks, the entire system was emptied of all liquid and then refilled with hot Water For Injection (WFI). The temperature of the WFI was superior to 70° C. The circulation loop flow was set at 583 l·h$^{-1}$kg$^{-1}$ during 10 mn (5 nm top/down flow and 5 mn down/top flow). The overpressure was of 300 mbars. Then, WFI was drained.

The system was refilled with WFI and a concentrated sodium hydroxide solution (10%) was added to reach a final concentration in the system of 2%. Then, the rotary lobe pump flow rate was progressively increased from 215 to 583 l·h$^{-1}$kg$^{-1}$ and maintained at this latter circulation loop flow rate during 30 nm (15 nm top/down flow and 15 nm down/top flow) at a temperature of 60° C.

Afterwards, one to four rinses were performed with ambient WFI at 583 l·h$^{-1}$kg$^{-1}$ and 200 mbars of overpressure. Each rinse lasted a minimum of 10 nm (5 nm top/down flow and 5 nm down/top flow).

Samples were transferred for pH, *Limulus Amebocyte* Lysate (LAL), Total organic carbon (TOC) and Bio Burden analyses after each rinsing-phase. LAL, TOC and Bio Burden were tested as described above, and pH was tested with paper pH. LAL, TOC, Bio Burden and pH indicate whether the system is clean or not. Preferably, pH shall be inferior to 8, LAL inferior to 0.5 EU·ml$^{-1}$, Bio Burden inferior to 5 CFU·ml$^{-1}$, and TOC inferior to 10 ppm before starting a new run.

The results of LAL, TOC, Bio Burden and pH analyses performed on samples transferred after each rinsing-phase are shown in table 2:

TABLE 2

| | pH | LAL | Bio Burden | TOC |
|---|---|---|---|---|
| 1$^{st}$ rinse | >10 | >2.5 | 0.44 | not measured |
| 2$^{nd}$ rinse | <10 | 0.0526 | 4 | not measured |
| 3$^{rd}$ rinse | <8 | 0.1837 | 5 | not measured |
| 4$^{th}$ rinse | <8 | 0.2168 | 3 | 0.4 |

The different analyses done after each rinsing-phase show that three rinses are sufficient to reach a pH value <8, a LAL value ≦0.5 EU·ml$^{-1}$ and a Bio Burden value ≦5 CFU·ml$^{-1}$. Accordingly, three rinsing phases allow reaching LAL, TOC, Bio Burden and pH that are conform to those required for starting a new run with the system.

3.2. Cumulative Productivity and Glucose Consumption Rate During Runs with Non-Recycled or with Recycled Fibra-Cel® Disks A subsequent run was performed with recycled Fibra-Cel® disks that had been rinsed three times. The day after the cleaning, the column containing recycled Fibra-Cel® disks was sterilized and kept sterile until start of the new run. The cumulative productivity and glucose consumption rate measured during this subsequent run are shown on FIGS. 1 and 2 respectively. The cumulative productivity and glucose consumption rate measured during runs with non-recycled Fibra-Cel® disks are also reported.

Figure 1:
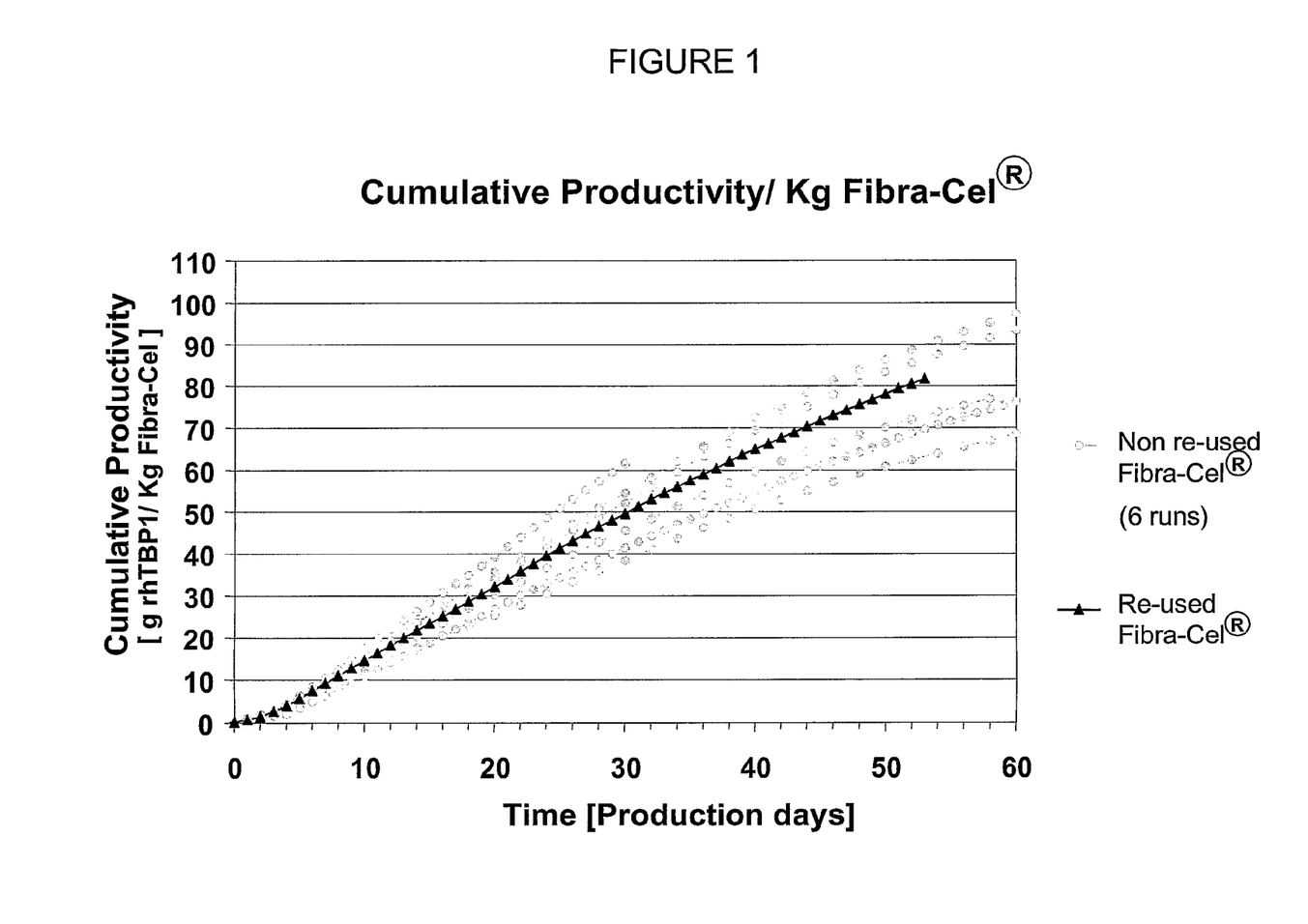
FIG. 1 compares the protein productivity measured when cultivating cells using non-recycled Fibra-Cel® disks (gray dots) or using Fibra-Cel® disks recycled according to a method of the present invention (black triangles).
Figure 2:
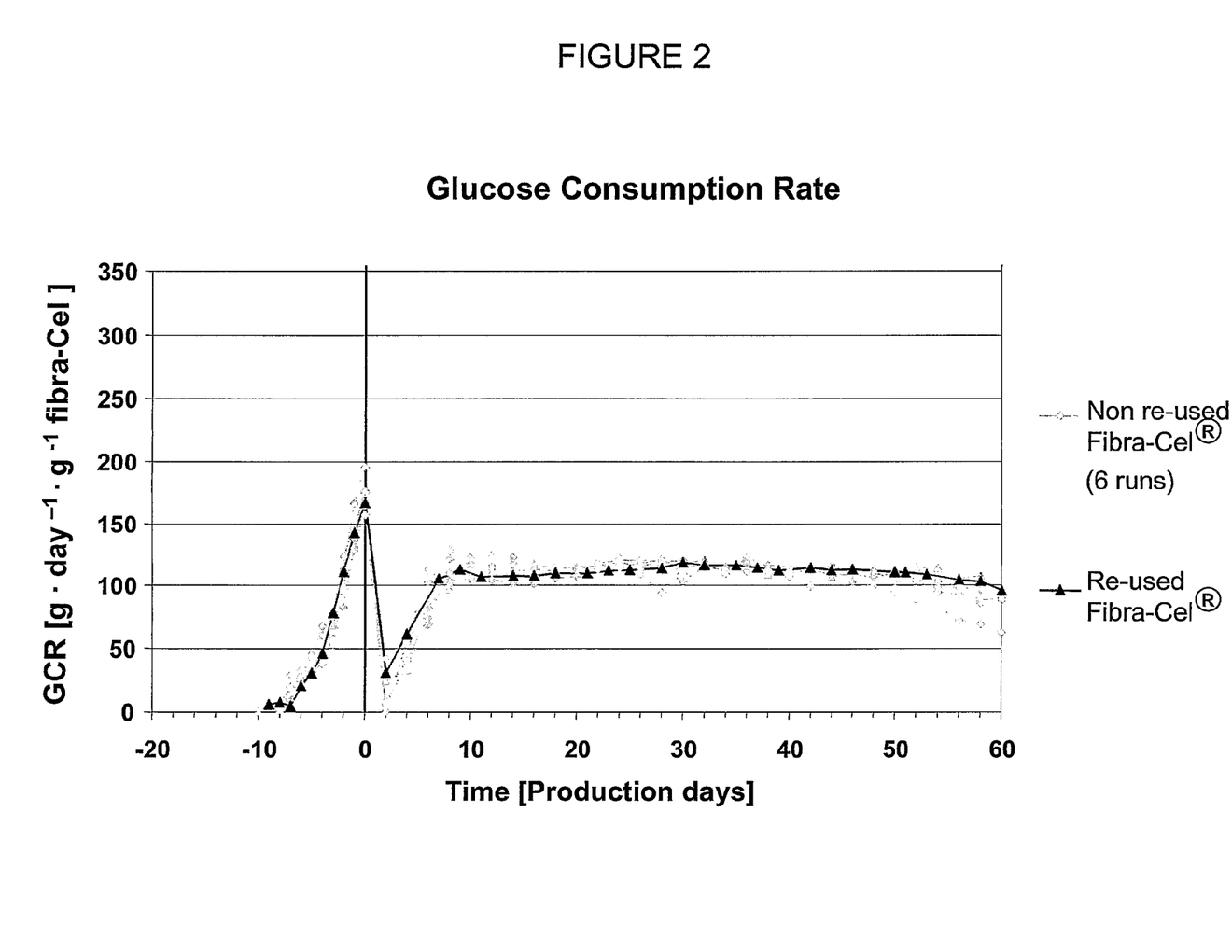
FIG. 2 compares the glucose consumption rate obtained when cultivating cells using non-recycled Fibra-Cel® disks (gray squares) or using Fibra-Cel® disks recycled according to a method of the present invention (black triangles).

As shown on FIGS. 1 and 2, the culture with recycled Fibra-Cel® disks had the same behavior as the culture with non-recycled Fibra-Cel® disks until the end of the run. Productivity and metabolism were similar. Specifically, the r-hTBP-1 productivity level obtained with recycled Fibra-Cel® disks is comparable to the r-hTBP-1 productivity level obtained with non-recycled Fibra-Cel® disks.

Example 4

Recycling Protocol and Results for Different Equipment Sizes

The systems comprised 40 liters or 350 liters bioreactors connected to external columns as described in Example 1.1.

At the end of a run carried out with non-recycled Fibra-Cel® disks, the entire system was emptied of all liquid and then refilled with hot Water For Injection (WFI). The temperature of the WFI was superior to 60° C. The circulation loop flow was set at 583 l·h$^{-1}$kg$^{-1}$ during 10 min. The overpressure was of 500 mbars. Then, WFI was drained.

The system was refilled with Purified Water (PW) containing a solution of sodium hydroxide solution (2%). The circulation loop flow was set at 583 l·h$^{-1}$kg$^{-1}$ during 30 min. at a temperature of 60° C.

Afterwards, one to four rinses were performed with ambient PW at 583 l·h$^{-1}$kg$^{-1}$ and 500 mbars of overpressure. Each rinse lasted a minimum of 10 min. A final rinse was performed in the same operational conditions with hot WFI.

Samples were transferred for pH, *Limulus Amebocyte* Lysate (LAL), Total organic carbon (TOC) and Bio Burden analyses after each rinsing-phase. LAL, TOC and Bio Burden were tested as described above, and pH was tested with paper pH. LAL, TOG, Bio Burden and pH indicate whether the system is clean or not. Preferably, pH shall be inferior to 8, LAL inferior to 0.25 EU·ml$^{-1}$, Bio Burden inferior to 10 CFU·100ml$^{-1}$, and TOC inferior to 10 ppm before starting a new run.

The results of LAL, TOC, Bio Burden and pH analyses performed on samples transferred after each rinsing-phase are shown in table 3:

TABLE 3

| Column volume (liter) | Rinsing cycles (-) | pH (-) | LAL (EU/ml) | Bioburden (CFU/100 ml) | TOC (ppm) |
|---|---|---|---|---|---|
| 60 | 3 | 7.5 | — | — | — |
| | 4 | 7.0 | — | — | 0.3 |
| | 5 | 7.0 | <0.25 | 0 | 0.3 |

TABLE 3-continued

| Column volume (liter) | Rinsing cycles (-) | pH (-) | LAL (EU/ml) | Bioburden (CFU/100 ml) | TOC (ppm) |
|---|---|---|---|---|---|
| 120 | 3 | 7.5 | — | — | 1.7 |
|  | 4 | 7.0 | — | — | 1.1 |
|  | 5 | 7.0 | <0.25 | 0 | 0.2 |
| 240 | 3 | 7.0 | — | — | 0.3 |
|  | 4 | 7.0 | — | — | 0.8 |
|  | 5 | 7.0 | <0.25 | 0 | 0.8 |

The different analyses done after each rinsing-phase show that three to five rinses are sufficient to reach a pH value <8, a LAL value $\leq 0.25$ EU·ml$^{-1}$ and a Bio Burden value $\leq 10$ CFU·100ml$^{-1}$. Accordingly, three rinsing phases allow reaching LAL, TOC, Bio Burden and pH that are conform to those required for starting a new run with the system.

The invention claimed is:

1. A method of recycling a solid support for anchorage-dependent cell cultivation within a system for cultivation of anchorage-dependent cells, the method comprising the steps of:
   a) providing an anchorage-dependent cell cultivation system, wherein the cell cultivation system comprises a solid support and a liquid;
   b) emptying the liquid from the anchorage-dependent cell cultivation system or removing said solid support from said cell cultivation system;
   c) after step (b), rinsing the solid support with an aqueous solution;
   d) after step (c), rinsing the solid support with a sodium hydroxide solution; and
   e) after step (d), rinsing the solid support with an aqueous solution to provide a recycled solid support,
wherein said solid support is made of a non-woven fibrous matrix bonded to a porous support sheet or is a microcarrier.

2. The method of claim 1, wherein said aqueous solution is water.

3. The method of claim 1, wherein said sodium hydroxide in said sodium hydroxide solution is at a concentration selected from the group consisting of:
   a) within a range of about 1% to about 3% sodium hydroxide;
   b) within a range of about 1.5% to about 2.5% sodium hydroxide; and
   c) about 2% sodium hydroxide.

4. The method of claim 1, wherein step (e) is performed at least three times.

5. The method of claim 4, wherein step (e) is performed three times.

6. The method of claim 4, wherein step (e) is performed five times.

7. The method of claim 1, wherein said aqueous solution in step (c) is Water For Injection (WFI).

8. The method of claim 1, wherein said aqueous solution in step (e) is Water For Injection (WFI).

9. The method of claim 4, wherein step (e) is performed with Purified Water (PW) except for the last repetition of step (e), which is performed with Water For Injection (WFI).

10. The method of claim 1, wherein said solid support is made of said non-woven fibrous matrix bonded to said porous support sheet.

11. The method of claim 10, wherein said solid support is a disk made of non-woven polyester bonded to a sheet of polypropylene mesh.

12. The method of claim 1, wherein said solid support is a microcarrier.

13. The method of claim 1, wherein said system further comprises a bioreactor.

14. The method of claim 13, wherein said system further comprises an external column connected to said bioreactor.

15. The method of claim 13, wherein said bioreactor contains an internal column.

16. The method of claim 14, wherein in step (a) said solid support is located within said-external column.

17. The method of claim 1, further comprising after step (e):
   f) sterilizing the cell culture system.

18. The method of claim 14, further comprising after step (e):
   f) sterilizing the external column.

19. The method of claim 1, wherein step (e) is carried out with a circulation loop flow selected from the group consisting of:
   a) within a range of about 500 l·h$^{-1}$kg$^{-1}$ to about 700 l·h$^{-1}$kg$^{-1}$;
   b) within a range of about 550 l·h$^{-1}$kg$^{-1}$ to about 650 l·h$^{-1}$kg$^{-1}$; and
   c) about 583 l·h$^{-1}$kg$^{-1}$.

20. The method of claim 1, wherein step (e) is carried out at ambient temperature.

21. The method of claim 1, wherein step (e) is carried out under an overpressure selected from the group consisting of:
   a) within a range of about 100 millibars to about 900 millibars;
   b) within a range of about 300 millibars to about 700 millibars; and
   c) about 500 millibars.

22. The method of claim 1, wherein step (e) is carried out for a duration selected from the group consisting of:
   a) within a range of about 5 minutes to about 30 minutes;
   b) within a range of about 5 minutes to about 20 minutes; and
   c) about 10 minutes.

23. The method of claim 1, wherein step (d) is carried out with a circulation loop flow set at a value selected from the group consisting of:
   a) within a range of about 500 l·h$^{-1}$kg$^{-1}$ to about 700 l·h$^{-1}$kg$^{-1}$;
   b) within a range of about 550 l·h$^{-1}$kg$^{-1}$ to about 650 l·h$^{-1}$kg$^{-1}$; and
   c) about 583 l·h$^{-1}$kg$^{-1}$.

24. The method of claim 1, wherein step (d) is carried out for a duration selected from the group consisting of:
   a) within a range of about 20 minutes to about 40 minutes;
   b) within a range of about 25 minutes to about 35 minutes; and
   c) about 30 minutes.

25. The method of claim 1, wherein step (d) is carried out at a temperature selected from the group consisting of:
   a) within a range of about 50° C. to about 70° C.;
   b) within a range of about 55° C. to about 65° C.; and
   c) about 60° C.

26. The method of claim 1, wherein step (c) is carried out at a temperature selected from the group consisting of:
   a) within a range of about 50° C. to about 70° C.;
   b) within a range of about 55° C. to about 65° C.; and
   c) about 60° C.

27. The method of claim 1, wherein step (c) is carried out under an overpressure selected from the group consisting of:
   a) within a range of about 100 millibars to about 900 millibars;

b) within a range of about 300 millibars to about 700 millibars; and c) about 500 millibars.

28. The method of claim 1, wherein step (c) is carried out for a duration selected from the group consisting of:

a) within a range of about 5 minutes to about 30 minutes;

b) within a range of about 5 minutes to about 20 minutes; and c) about 10 minutes.

* * * * *

UNITED STATES PATENT AND TRADEMARK OFFICE
CERTIFICATE OF CORRECTION

PATENT NO. : 8,080,419 B2
APPLICATION NO. : 10/580777
DATED : December 20, 2011
INVENTOR(S) : Alain Bernard et al.

Page 1 of 2

It is certified that error appears in the above-identified patent and that said Letters Patent is hereby corrected as shown below:

Column 1,
Line 3,
"PROCESS FOR RECYCLING SOLID SUPPORTS FOR CULTIVATION OF
ANCHORAGE-DEPENDENT CELLS

FIELD OF THE INVENTION"

should read

--PROCESS FOR RECYCLING SOLID SUPPORTS FOR CULTIVATION OF
ANCHORAGE-DEPENDENT CELLS

CROSS-REFERENCE TO RELATED APPLICATIONS
This application is the U.S. national stage application of International Patent
Application No. PCT/EP2004/053133, filed November 26, 2004, which claims the
benefit of U.S. Provisional Patent Application No. 60/526,414, filed December 2,
2003, the disclosures of which are hereby incorporated by reference in their entireties,
including all figures, tables and amino acid or nucleic acid sequences.

FIELD OF THE INVENTION--.

Line 9, "so lid supports" should read --solid supports--.
Line 53, "such as, e.g., e.g.," should read --such as, e.g.,--.

Column 2,
Line 34, "to the u se" should read --to the use--.

Column 3,
Line 33, "15% to" should read --1.5% to--.

Signed and Sealed this
Fourth Day of September, 2012

David J. Kappos
*Director of the United States Patent and Trademark Office*

Column 8,
Line 63, "column The" should read --column. The--.

Column 9,
Lines 61-62, "150 l·h$^{-1}$kg$^{-1}$ to 800 l·h$^-$ $_1$kg$^{-1}$ when" should read --150 l·h$^{-1}$kg$^{-1}$ to 800 l·h$^{-1}$kg$^{-1}$ when--.

Column 10,
Lines 1-2, "(30 l·day$^-$ $_1$kg$^{-1}$" should read --(30 l·day$^{-1}$kg$^{-1}$--.

Column 12,
Line 3, "are conform to" should read --are conformed to--.